US007190989B1

(12) United States Patent
Swanson et al.

(10) Patent No.: US 7,190,989 B1
(45) Date of Patent: *Mar. 13, 2007

(54) MULTI-CHANNEL FLEXIBLE BIO-PROBE AND METHOD OF MAKING THE SAME

(75) Inventors: John W. Swanson, Portland, OR (US); Norman M. Hill, Bothell, WA (US); Jerome J. Boogaard, Portland, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 312 days.

This patent is subject to a terminal disclaimer.

(21) Appl. No.: 10/760,856

(22) Filed: Jan. 20, 2004

Related U.S. Application Data

(60) Continuation-in-part of application No. 10/429,652, filed on May 5, 2003, now Pat. No. 6,892,438, which is a division of application No. 09/886,322, filed on Jun. 21, 2001, now Pat. No. 6,560,472.

(51) Int. Cl.
*A61B 5/0478* (2006.01)

(52) U.S. Cl. ...................... 600/378; 607/116

(58) Field of Classification Search ............... 600/378; 607/116
See application file for complete search history.

(56) References Cited

U.S. PATENT DOCUMENTS

| 4,461,304 A | * | 7/1984 | Kuperstein | ................ 600/378 |
| 5,524,338 A | * | 6/1996 | Martyniuk et al. | ........... 29/825 |
| 6,560,472 B2 | * | 5/2003 | Hill et al. | ................... 600/378 |

* cited by examiner

*Primary Examiner*—Lee S. Cohen
(74) *Attorney, Agent, or Firm*—Law Office of Timothy E. Siegel; Timothy E. Siegel

(57) ABSTRACT

A bio-probe having a base and a tip, and comprising a longitudinal core of substantially rigid material. On the core, there is a first layer of dielectric material, supported by and substantially circumferentially surrounding the core. Also, a set of conductors, each conductor extending longitudinally along the first layer of dielectric material and a second layer of dielectric material, substantially covering each of the set of conductors. For each of the conductors, an aperture is defined through the second layer of dielectric material to the conductor, thereby defining an electrode. In one preferred embodiment of this aspect, the first layer of insulative material is in the form of a tube and wherein the core is removable from the tube.

8 Claims, 3 Drawing Sheets

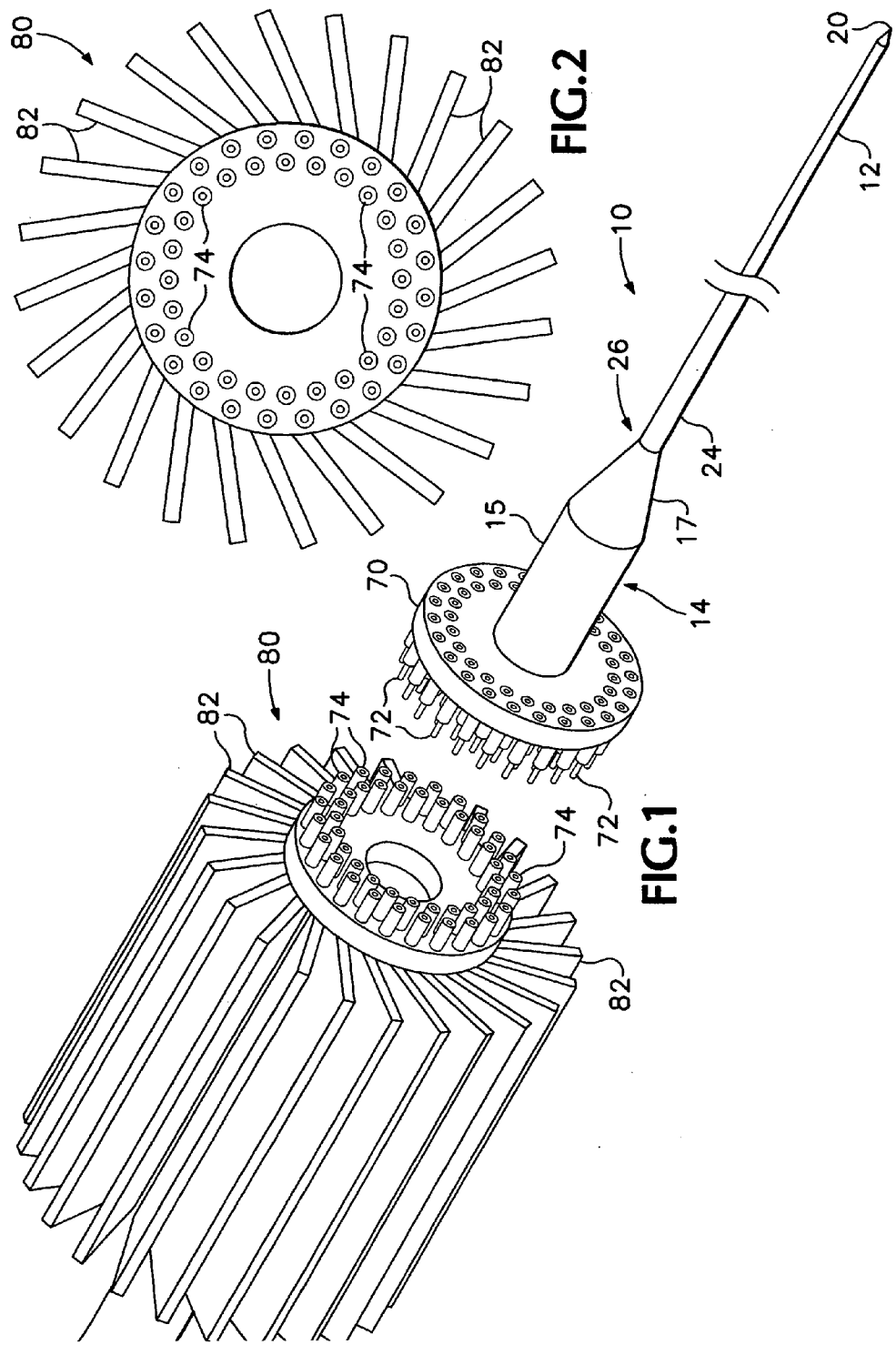

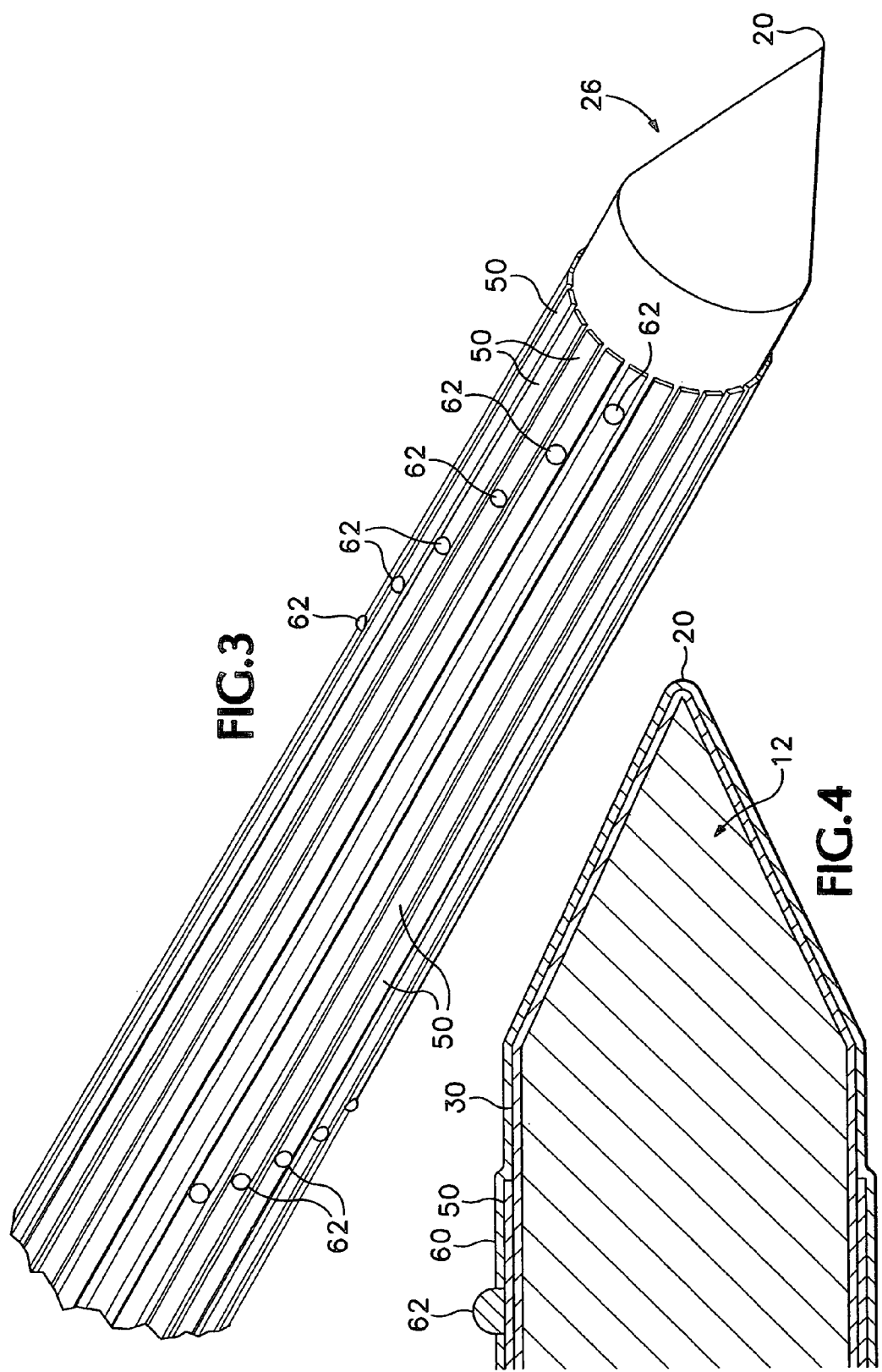

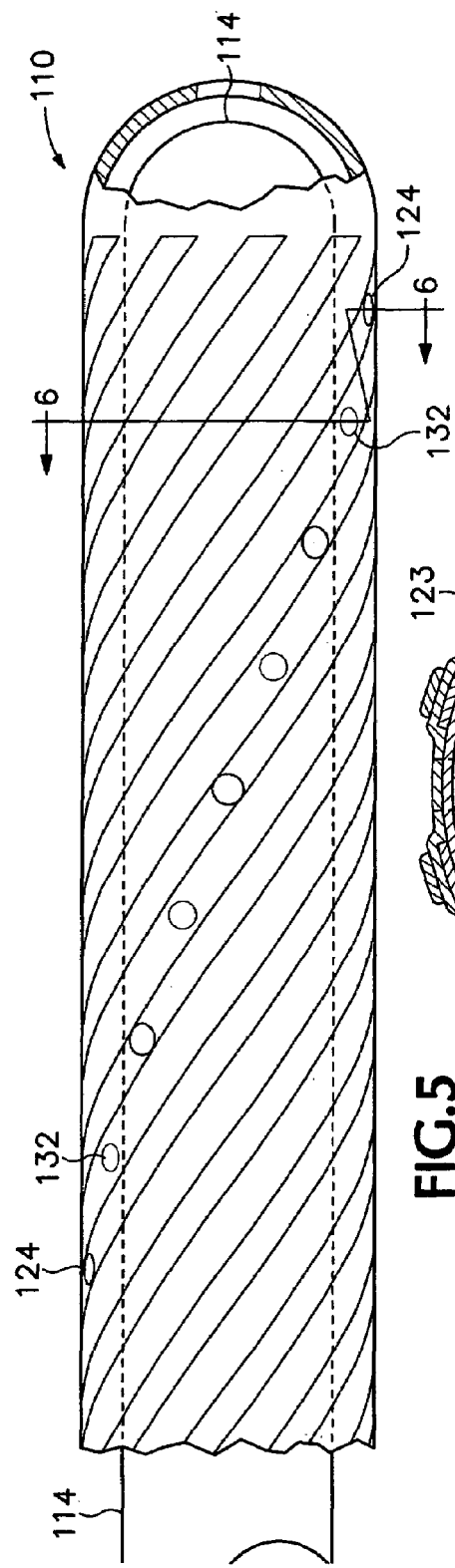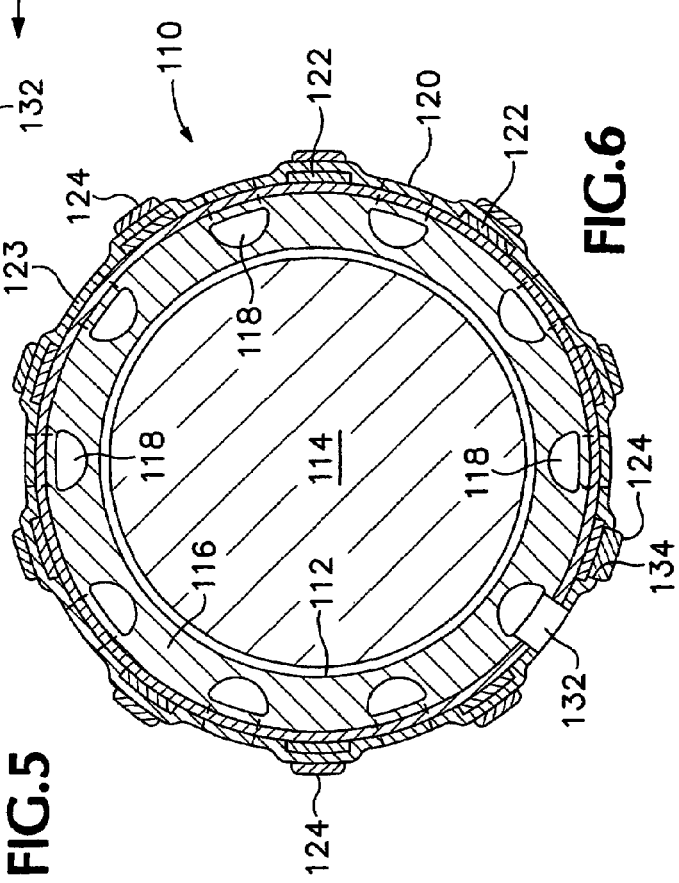

MULTI-CHANNEL FLEXIBLE BIO-PROBE AND METHOD OF MAKING THE SAME

RELATED APPLICATION

This application is a continuation-in-part of application Ser. No. 10/429,652 filed May 5, 2003, now U.S. Pat. No. 6,892,438, which is a divisional of Ser. No. 09/886,322, filed Jun. 21, 2001, now U.S. Pat. No. 6,560,472, issued May 6, 2003.

STATEMENT OF GOVERNMENTAL SUPPORT

This invention was made with government support under grant No. 1R43MH59502-01 awarded by the Small Business Research Program of the Department of Health and Human Services of the Public Health Service. The government has certain rights in the invention.

BACKGROUND OF THE INVENTION

The construction of a brain probe assembly to be employed in brain research is quite challenging from both a structural and an electrical standpoint.

Structurally, probes must not fray or in any way come apart when pushed through the dura, a tough membrane covering the brain, and other brain tissue. Probe should have enough strength and rigidity to broach the dura without the need for assistance by, for example, a guide tube or an initial incision.

Moreover, probes must not break, running the risk of leaving a fragment in the brain. Also, they must not cause undue damage to tissue at the sensing site. Inevitably, the tissue separating the sensing site from the brain exterior will suffer some damage as a probe is pushed to its destination. A small cross-section probe, however, may cause less damage as it is pushed to its destination. It is best to avoid having a sharp tip or any sharp edges, however, as this could cause blood vessels to be severed during the insertion process.

Electrically, one should note that the electric field signals in the brain, which the probe is designed to detect, are typically of the order of 100 to 500 μvolts. The low amplitude of these signals makes it necessary to amplify them as physically close as possible to their source. In fact, the signals involved are so minute that variations in circuit geometry could well affect significantly the detection processing of the signals. It is also highly desirable to minimize cross-talk between any two signals.

Additionally, it is generally advantageous for a brain probe to become flexible after being inserted so that the motion of the brain within the brain pan is not resisted by the probe. In the worst case this could cause tissue tearing. To insert a brain probe, however, it is better for the probe to be in a rigid state. Given the tight geometries allowable for brain probe design, these requirements are difficult to meet simultaneously.

SUMMARY OF THE INVENTION

In a first separate aspect, the present invention is a bio-probe having a base and a tip, and comprising a longitudinal core of substantially rigid material. On the core, there is a first layer of dielectric material, supported by and substantially circumferentially surrounding the core. Also, a set of conductors, each conductor extending longitudinally along the first layer of dielectric material and a second layer of dielectric material, substantially covering each of the set of conductors. For each of the conductors, an aperture is defined through the second layer of dielectric material to the conductor, thereby defining an electrode. In one preferred embodiment of this aspect, the first layer of insulative material is in the form of a tube and wherein the core is removable from the tube.

In a second separate aspect, the present invention is a method of producing a bio-probe, starting with a longitudinal core of substantially rigid material, the core having a base and a tip. A coating of dielectric material, is provided about the core. The dielectric material is coated with a first layer of conductive material and the conductive material is divided into longitudinal traces, extending from the base, to a region close to the tip. The conductive material is coated with a second layer of dielectric material and portions of the second layer of dielectric material are removed to form apertures to the conductive material, thereby forming electrodes.

In a third separate aspect, the present invention is a bio-probe having a base and a tip, and comprising a longitudinal core of substantially rigid material. Also, a layer of dielectric material is supported by and substantially circumferentially surrounds the core, the layer defining at least one lumen, having an opening near the tip of the bio-probe.

The foregoing and other objectives, features and advantages of the invention will be more readily understood upon consideration of the following detailed description of the preferred embodiment(s), taken in conjunction with the accompanying drawings.

BRIEF DESCRIPTION OF THE DRAWINGS

FIG. 1 is an exploded perspective view of bio-probe assembly according to the present invention.

FIG. 2 is a front view of the circuit card assembly of the bio-probe assembly of claim 1.

FIG. 3 is an expanded perspective view of the tip of the bio-probe assembly of FIG. 1.

FIG. 4 is a greatly expanded cross-sectional view of the tip of the bio-probe assembly of FIG. 1.

FIG. 5 is a side view of an alternative embodiment of a bio-probe, according to the present invention.

FIG. 6 is a cross-sectional view of the bio-probe of FIG. 5, taken along line 6—6 of FIG. 5.

DETAILED DESCRIPTION OF THE PREFERRED EMBODIMENT

A preferred embodiment of a brain probe or bio-probe assembly 10, according to the present invention is composed of a probe core 12 and a handle core 14. The probe core 12 is made of tungsten, chosen for its material stiffness and tensile strength. Probe core 12 is preferably straight. To achieve this end, a straightening machine that pulls on core 12, thereby creating tensile stress and annealing core 12 may be used. During further operations, a vacuum chuck may be used to hold core 12 in place. A tip or distal end 20 of probe core 12 has a diameter of 200 microns (8.0 mils) and a base or proximal end 24 of core 12 has a diameter of 600 microns (24 mils). In addition, core 12 is 89 mm (3.5") long. The tip 20 is preferably formed by way of centerless grinding. Probe core 12 should be electro polished so that the deposition of materials onto it (see below) can be accomplished efficiently and so that the finished assembly 10 can pass through brain tissue as smoothly as possible. Alternatively, probe core 12 can be left in a comparatively rough state and coated with a coat of epoxy that is thick enough to minimize capacitance between core 12 and the traces 50 (discussed below). The comparatively rough state of the probe core actually helps to effect the binding of the epoxy to the probe core. One type of epoxy that can be used is the epoxy 377 discussed further below.

For ease of assembly and so that operating personnel may more easily handle assembly 10, the handle core 14 is expanded in cross-section relative to probe core 12. Although the handle core 14 is preferably a unitary piece of medical grade 304 stainless steel, it may be conceptually divided into a cylinder 15, having a diameter of 4.826 mm (0.19"), and a frustum 17. The frustum 17 tapers inwardly at 150 angle from the sides of cylinder 15. A 600 µm (24 mil) aperture (not shown) at the narrow end of frustum 17 permits introduction of the base of probe core 12, after which probe core 12 is joined to handle core 14, by way of an epoxy, to form joint core 26. The epoxy used must be conductive, so that the probe core 12 is grounded to the base core 14, and preferably heat resistant, so that it withstands the sterilization process that the probe 10 generally should undergo in use. It must also be able to withstand the different degrees of expansion that stainless steel and tungsten undergo during the sterilization process. An epoxy that is available from Epoxy Technology, Inc. of Billerica, Mass., under the designation E3084 appears to meet these requirements. In an alternative preferred embodiment, the probe core 12 is laser-welded to the base core 14.

After joint core 26 is produced, it is dip coated with a dielectric epoxy, which has been premixed with a surfactant to promote an even coating, to form an insulating coat 30. The desirable characteristics for an epoxy to be used are biocompatibility, heat tolerance to withstand the sterilization process, low viscosity to produce a thin film, a heat accelerated cure and a high bulk resistivity and a low dielectric coefficient to avoid electrical losses and withstand electrostatic charges. One epoxy that appears to meet these requirements is the epoxy #377 noted earlier. A suitable surfactant is available as FC-430 from 3M of St. Paul, Minn. Alternatively, acrylated epoxy could be used. For coat 30, this material could have the composition, noted in Table I, below, in parts per hundred resin (PHR):

TABLE I

| Substance | Proportion | Source, Contact Information |
|---|---|---|
| Photomer 3015 | 100 PHR | Cognis Corp., http://www.na.cognis.com/northamerica/nacognis.html |
| TMPEOTA, (Trimethylolpropane triacrylate SR-351) | 50 PHR | Sartomer Company, Inc., http://www.sartomer.com |
| R-812S (fumed silica) | 10 PHR | Degussa Corp., http://www.degussa.com/en/home.html |
| MIBK (Methyl Isobutyl Keytone) | 20 PHR | Aldrich Corp., http://www.sigmaaldrich.com/Brands/Aldrich.html |
| Darocure 1173 (Photoinitiator) | 2.6 PHR | EM Chemicals Corp., http://www.emdchemicals.com/corporate/emd_corporate.asp |

In an additional preferred embodiment quartz crystal, glass or a similar dielectric material is vacuum deposited to form coat 30. In this preferred embodiment, in order to gain adherence, however, a 200 Å coat of chrome (not shown) is first applied, also through vacuum deposition on core 26 to promote the adhesion of coat 30. The thickness of coat 30 is chosen to minimize the capacitance between core 26 and the conductive traces 50 (see below) deposited over it.

On top of coat 30, a 0.5 µm thick plate of conductive material (not shown as such but later rendered into a set of traces 50) is, preferably, vacuum deposited. This plate 50 also may be adhered by way of a 200 Å layer of vacuum deposited chrome (not shown). Plating 50 must be highly conductive and, if vacuum coating is used, must be an element of the periodic table. Accordingly, gold, platinum and iridium are among the materials that may be used. Other deposition techniques, such as chemical deposition, may permit the application of other highly conductive materials, such as a conductive polymer. The material used to create plating 50 must also be susceptible to removal by laser ablating or an etching process.

Next, plate 50 is sectioned into 24 longitudinal traces 50 (other numbers of traces 50 are possible) extending from approximately the tip 20 to the proximal end of base core 14. Accordingly, near the tip 20 the traces 50 have a pitch of about 27 µm, near the base 24 have a pitch of about 80 µm at the proximal end of handle 14 have a pitch of about 630 µm. Of particular utility for performing the task of sectioning the conductive plate into traces 50 is a frequency multiplied ND:YAG laser, which can cut kerfs to separate the traces on the order of 5–10 µm width.

In one preferred embodiment there are just four traces 50. Using this embodiment a compound probing device may be built that incorporates an array of probe assemblies 10 to sense and/or stimulate a number of neural sites separated not just in depth, but also transversely to probe assembly 10 longitudinal dimension.

Next, the conductive traces 50 are coated with an outer layer 60 of high coefficient dielectric material. An additional dip coat of epoxy #377 is one way of accomplishing this. As an alternative, an acrylated epoxy urethane may be used, similar to the acrylated epoxy that my be used for layer 30, and described by Table II, below:

TABLE II

| Substance | Proportion | Source, Contact Information |
|---|---|---|
| Photomer 3015 | 100 PHR | Cognis Corporation, http://www.na.cognis.com/northamerica/nacognis.html |
| TMPEOTA, (Trimethylolpropane triacrylate SR-351) | 50 PHR | Sartomer Company, Inc., http://www.sartomer.com |
| RX 03961 (acrylated urethane) | 32 PHR | UCB Radcure, Inc., http://www.chemicals.ucb-group.com/default2.html |
| R-812S (fumed silica) | 10 PHR | Degussa Corp., http://www.degussa.com/en/home.html |
| MIBK (Methyl Isobutyl Keytone) | 63 PHR | Aldrich Co., http://www.sigmaaldrich.com/Brands/Aldrich.html |
| Darocure 1173 (Photoinitiator) | 2.6 PHR | EM Chemicals, http://www.emdchemicals.com/corporate/emd_corporate.asp |

Another method is a vacuum deposition of glass or quartz crystal placed, again over an intermediate 200 Å layer of chrome. Dielectric layer 60 preferably has a thickness of from 10 to 40 um to avoid damage by static electric discharge. A laser is used to ablate this outer layer to create several apertures extending through layer 60, having a diameter of about 10 µm at each prospective microelectrode site. A platinum-iridium electrode or neural contact site 62 is built up, preferably by electroplating, at each of these sites. Other materials that could be used for the neural contact sites 62 are platinum (not mixed with iridium), iridium, and oxidized iridium, which is also referred to as iridium black, and intrinsically conductive polymers, such as a doped polypyrrole.

Base 14 is attached to a plate 70 that includes outwardly extending conductive traces (not shown) that connect traces 50 to a set of connector pins 72. In turn, a set of connectors 72 on plate 70 attach to a matching set of connectors 74 on a circuit card assembly 80. Assembly 80 includes a set of 24 circuit cards 82, one for each trace, each bearing an identical amplification circuit for processing each signal from each trace 50 in an identical manner.

The advantages of the above described preferred embodiment should now be apparent. Probe assembly 10 is strong, smooth and sleek, for moving through brain tissue to the site of interest. The cross capacitance between traces 50 is minimized due to the shape of the traces 50, which are curved solid rectangles, on the order of 0.5 um thick but varying between 10 um and 50 um wide. Finally, identical circuits 82 ensure equal treatment for each trace signal.

An alternative preferred embodiment of a bio-probe 110 according to the present invention is shown in FIGS. 5 and 6. Bio-probe 110 differs from bio-probe 10 in that it is made of flexible material and defines an inner lumen 112, for accepting a rigid insert 114. Rigid insert 114 permits bio-probe 110 to be pushed through body tissue, for example brain tissue. Insert 114 is then removed, so that as the probe recipient moves about with the probe installed, the flexible bio-probe 110 will not tear into brain tissue, as the brain moves about slightly in the brain pan.

To manufacture bio-probe 110, a mandrel, very similar in nature to insert 114 is used. A tube 116 of flexible dielectric material, for example, polyimide is provided and fit over mandrel 114. Tube 116 defines ten lumens 118, the purpose of lumens 118 will be described later. The production of tube 116 may be effected by molding of polymeric resin. For example tube 116 could be produced by vacuum molding of polyimide resin.

A layer of conductive material, for example gold, is then deposited by, for example, vapor deposition or sputtering. The original deposition of thin layer of conductive material may be followed by an electroplating stage, in which a thicker layer of conductive material is built up on the seed layer.

Next a set of kerfs 120 are created, thereby creating a set of separated conductive traces 122. Kerfs 120 may be formed by laser machining as noted above in reference to bio-probe 10 or through a photolithographic technique. The photolithographic technique could include a mask being pulled across a light source as bio-probe 10, coated with photo resist, is rotated to expose different sections. Other than this rotation technique, the photolithography would be relatively standard, with either positive or negative photo resist being used, and the metal being etched away in places where the developed photo resist has been removed.

Next, an additional layer 123 of dielectric material is coated over traces 122. Apertures 132 are created to lumens 118 and apertures 134 are created to traces 122 by the use of an ND:YAG frequency multiplied laser. Finally, platinum-iridium electrodes 124 are built up in apertures 134. These electrodes are used to stimulate brain cells and sense brain activity. Lumens 118 and apertures 132 are used in the delivery of substances, for example, a medicine or a stimulant to brain tissue. Apertures 132 and electrodes 124 can be used in tandem with a liquid substance administered through apertures 132 and the resultant effect measured by electrodes 124.

The terms and expressions that have been employed in the foregoing specification are used as terms of description and not of limitation. There is no intention, in the use of such terms and expressions, of excluding equivalents of the features shown and described or portions thereof, it being recognized that the scope of the invention is defined and limited only by the claims which follow.

The invention claimed is:

1. A bio probe having a base and a tip, and comprising:
   (a) a longitudinal core of substantially rigid material, wherein the longitudinal core is substantially circular in cross-section from the base to the tip of the core and the longitudinal core tapers from the base to the tip;
   (b) a first layer of dielectric material, supported by and substantially circumferentially surrounding said core;
   (c) a set of conductors, each conductor extending longitudinally along said first layer of dielectric material, the set of conductors substantially circumscribing the core, wherein said set of conductors are made from conductive material that is deposited directly upon said first layer of dielectric material and each adjacent pair of conductors of said set of conductors is mutually separated by a trench running longitudinally along the length of said bio-probe;
   (d) a second layer of dielectric material, substantially covering each of said set of conductors; and
   (e) for each said conductor, an aperture defined through said second layer of dielectric material to said conductor, thereby defining an electrode.

2. The bio-probe of claim 1, wherein said first layer of dielectric material is deposited directly upon said core.

3. The bio-probe of claim 1, wherein said second layer of dielectric material is made of epoxy resin.

4. The bio-probe of claim 1, wherein each conductor of said set of conductors is roughly rectangular in cross section and is each more than three times as wide as it is thick and is substantially conformal over said first layer of dielectric material.

5. The bio-probe of claim 1, wherein said core is comprised of tungsten.

6. The bio probe of claim 1, wherein said apertures are filled with conductive material.

7. The bio-probe of claim 1, wherein said second dielectric layer has an exterior surface and said apertures are filled with conductive material that extends onto and beyond said exterior surface of said second dielectric layer.

8. The bio probe of claim 1, wherein said core, said set of conductors and said first and second layers of dielectric material form a first portion that has a base and further including a second portion having a tip and a base and wherein said tip of said second portion is adapted to attach to said base of said first portion.

* * * * *

UNITED STATES PATENT AND TRADEMARK OFFICE
CERTIFICATE OF CORRECTION

PATENT NO. : 7,190,989 B1 Page 1 of 1
APPLICATION NO. : 10/760856
DATED : March 13, 2007
INVENTOR(S) : Swanson et al.

It is certified that error appears in the above-identified patent and that said Letters Patent is hereby corrected as shown below:

Column 3, line 13, Change:
150 to 15°

Signed and Sealed this

Twenty-eighth Day of August, 2007

JON W. DUDAS
*Director of the United States Patent and Trademark Office*